(12) United States Patent
Tschekalinskij et al.

(10) Patent No.: US 10,139,339 B2
(45) Date of Patent: Nov. 27, 2018

(54) COLOUR SENSOR WITH ANGLE-SELECTIVE STRUCTURES

(71) Applicant: FRAUNHOFER-GESELLSCHAFT ZUR FOERDERUNG DER ANGEWANDTEN FORSCHUNG E.V., Munich (DE)

(72) Inventors: Wladimir Tschekalinskij, Nuremberg (DE); Stephan Junger, Bubenreuth (DE); Nanko Verwaal, Herzogenaurach (DE); Norbert Weber, Weissenohe (DE)

(73) Assignee: FRAUNHOFER-GESELLSCHAFT ZUR FOERDERUNG DER ANGEWANDTEN FORSCHUNG E.V., Munich (DE)

( * ) Notice: Subject to any disclaimer, the term of this patent is extended or adjusted under 35 U.S.C. 154(b) by 0 days.

(21) Appl. No.: 15/600,841

(22) Filed: May 22, 2017

(65) Prior Publication Data

US 2017/0336317 A1    Nov. 23, 2017

(30) Foreign Application Priority Data

May 23, 2016    (DE) .......................... 10 2016 208 841

(51) Int. Cl.
*G01N 21/25*    (2006.01)
*G01N 21/27*    (2006.01)
(Continued)

(52) U.S. Cl.
CPC .......... *G01N 21/255* (2013.01); *G01J 3/0289* (2013.01); *G01J 3/2803* (2013.01);
(Continued)

(58) Field of Classification Search
CPC ..... G01N 21/255; G01N 21/251; G01N 21/27
(Continued)

(56) References Cited

U.S. PATENT DOCUMENTS

| 8,976,357 B2 * | 3/2015 | Uematsu | ................... G01J 1/06 356/416 |
| 2006/0113622 A1 | 6/2006 | Adkisson et al. | ............ 257/443 |

(Continued)

*Primary Examiner* — Hina F Ayub
(74) *Attorney, Agent, or Firm* — Renner Kenner Greive Bobak Taylor & Weber (57) ABSTRACT

The present invention relates to a color sensor having at least one photosensitive element, in front of which a layer stack of dielectric layers and structured metal layers is constructed, and at least one color filter, through which optical radiation incident on a light input side of the color sensor is filtered before it reaches a photosensitive surface of the photosensitive element. In the suggested color sensor, an array of angle-selective passageways is provided for the optical radiation between the light input side and the photosensitive surface, and each passageway only allows parts of the optical radiation incident on the light input side of the color sensor within a limited angle of incidence range relative to an axis extending perpendicularly to the colour filter to pass through to the photosensitive surface. When the color sensor is manufactured with semiconductor technology, it enables the angle-selective structures to be integrated in the CMOS layer stack. In this way, ultra-flat color sensors can be made.

15 Claims, 7 Drawing Sheets

(51) Int. Cl.
*G01J 3/51* (2006.01)
*G01J 3/02* (2006.01)
*G01J 3/28* (2006.01)

(52) U.S. Cl.
CPC ............ *G01J 3/513* (2013.01); *G01N 21/251* (2013.01); *G01N 21/27* (2013.01)

(58) Field of Classification Search
USPC .......................................................... 356/416
See application file for complete search history.

(56) References Cited

U.S. PATENT DOCUMENTS

| | | |
|---|---|---|
| 2008/0036023 A1 | 2/2008 | Park .............................. 257/432 |
| 2009/0170236 A1* | 7/2009 | Jung ................. H01L 27/14687 438/98 |
| 2009/0295953 A1 | 12/2009 | Nozaki ......................... 348/294 |
| 2010/0133643 A1* | 6/2010 | Park ................. H01L 27/14603 257/461 |
| 2010/0242768 A1 | 9/2010 | Huber ........................... 101/484 |
| 2013/0130400 A1* | 5/2013 | Harbers .................... G01J 3/28 436/171 |
| 2014/0197301 A1 | 7/2014 | Velichko et al. .......... 250/208.1 |
| 2017/0077163 A1* | 3/2017 | Chou ................ H01L 27/14627 |
| 2017/0160134 A1* | 6/2017 | Ross ......................... G01J 3/26 |

* cited by examiner

COLOUR SENSOR WITH ANGLE-SELECTIVE STRUCTURES

TECHNICAL FIELD

The present invention relates to a colour sensor having at least one photosensitive element, in front of which a layer stack of dielectric layers and structured metal layers is constructed, and at least one colour filter, through which optical radiation incident on a light input side of the colour sensor is filtered before it reaches a photosensitive surface of the photosensitive element.

Optical colour sensors are used for example in colorimeters for colour recognition in printing machines and in the textile industry, to control the colour of LED lamps, or in analytics. As a rule, they use interference filters or plasmonic filters as colour filters in front of the photosensitive element.

Such filters are strongly affected by angle. If radiation does not strike them perpendicularly, the centre wavelength of the passband of the filters shifts into the short-wave band. This shift is determined by the angle of incidence, the refractive index of the filter and the wavelength:

$$\lambda_1 = \lambda_0 (1 - \sin_2 \theta / n^2)^{1/2}$$

in which $\theta$ corresponds to the angle of incidence, $\lambda_1$ to the peak wavelength at angle of incidence $\theta$, $\lambda_0$ to the peak wavelength at perpendicular incidence ($\theta = 0°$) and n to the effective refractive index of the colour filter. In plasmonic filters, this effect is more pronounced than with interference filters. The filter characteristic is broader and the transmittance in the passband is attenuated. This behaviour affects the accuracy of measurements taken using such a colour sensor.

PRIOR ART

In order to ensure a high level of measurement accuracy, angle-selective structures are used in colour sensors which only permit optical radiation that arrives at the light input side of the colour sensor within a correspondingly small incidence angle range to reach the photosensitive element. This can be achieved with an additional mechanical assembly on the colour sensor. Such an assembly very often consists of a duct with a small opening that defines the maximum angle of incidence. However, in a colour sensor that has been manufactured entirely on the basis of semiconductor technology, the mechanical assembly is much larger than the colour sensor itself. It is very difficult to integrate an angle-selective structure of such kind with semiconductor technology for photosensitive elements with a relatively large photosensitive surface, because in this case the CMOS layer stack, which normally has a thickness≤10 µm above the photosensitive surface, would have to be about 1 mm or higher in order to assure a good filter effect. However, unlike image sensor elements in a RGB camera, optical colour sensors are used for absolutely accurate measurement of colour temperature and colour location, and they therefore need a correspondingly larger-area photosensitive element with low noise and high sensitivity. Accordingly, photodiodes which are used to measure colour in optical colour sensors typically have a photosensitive surface area≥20×20 µm. In contrast to this, the image sensor elements or pixels in RGB cameras are typically considerably smaller and have a pixel size of 5×5 µm. In image sensors of this kind for RGB cameras, "crosstalk filters" in the form of waveguides or microlenses are used to prevent crosstalk among the individual pixels.

In this context, the purpose is not to limit the angle of incidences for the purpose of spectral filtering, but simply to avoid crosstalk among the individual pixels.

Thus for example, US 2006/0113622 A1 describes a structure for avoiding crosstalk between image sensor elements, in which an optical waveguide is embedded in the layer stack of dielectric layers and structured metallic layers above each photodiode, and which prevents crosstalk with adjacent image sensor elements by means of a boundary consisting of a reflective or absorbing layer.

From US 2009/0295953 A1, an image sensor having an array of image sensor elements is known in which an aperture arrangement is formed for each image sensor element by structuring of the metallic layers in the CMOS-layer stack, which aperture arrangement is intended to have a lens effect which focuses the incident radiation on the respective photodiode of the image sensor element.

An image sensor having an array of image sensor elements in which a light waveguide for each image sensor element is integrated in the CMOS layer stack is known from US 2014/0197301 A1. It is also suggested to create electrical through-connections in the dielectric layers of the layer stack in such manner as to form one or more closed rings around the respective waveguide. These measures are intended to prevent crosstalk among the individual image sensor elements.

These crosstalk filters used in camera image sensors for avoiding crosstalk can be integrated in the CMOS layer stack for the small photosensitive surfaces of individual image sensor elements or pixels present there. They also only have to prevent crosstalk between the individual pixels, and they are not intended to limit the angle of incidence to provide the most accurate spectral filtering possible. In order to achieve such a limitation of the angle of incidence for a large-area photodiode such as is used in optical colour sensors, the CMOS layer stack would have be made many times higher.

DE 10 2010 011 577 A1 describes a solution approach for angle-dependent colour correction for colour measurement with colour sensors that does not require the use of an additional angle-selective structure on the colour sensor. The entire colour correction is carried out by a computer. This is a good solution for printing machines, in which the angle of incidence the light can be restricted by additional optical elements. In general practice, however, it is still difficult to use the device for measuring because the useful signal (light with angle of incidence<20°)has to be filtered out of the total signal (light with angle of incidence>20°). Usually, the entire angle spectrum from ±80° reaches the colour sensor.

The object of the present invention consists in describing a colour sensor having angle-selective structures, which sensor may be of thin construction and enables highly accurate measurements. In a preferred variant, the colour sensor should be completely producible, together with the angle-selective structures, in semiconductor technology.

PRESENTATION OF THE INVENTION

This object is achieved with the colour sensor according to patent claim 1. Advantageous variants of the colour sensor are subject matter of the dependent claims or are revealed in the following description and exemplary embodiments thereof.

The suggested colour sensor includes at least one photosensitive element with a photosensitive surface area of preferably ≥10×10 µm, in front of which a layer stack of dielectric layers and structured metallic layers is formed, and at least one colour filter, through which optical radiation incident on the light input side of the colour sensor is filtered before it reaches the photosensitive surface of the photosensitive element. The colour filter is arranged between the light input side of the colour sensor and the photosensitive surface. It may be arranged on the layer stack or between the layer stack and the photosensitive surface or it may also be integrated in the layer stack. In this context, the photosensitive element preferably has the form of a photodiode. The suggested colour sensor differs from other devices of its kind in that an array of angle-selective passageways is provided for the optical radiation between the light input side and the photosensitive surface, each passageway only allowing parts of the optical radiation that reach the light input side of the colour sensor within a limited angle of incidence range relative to an axis extending perpendicularly to the colour filter to pass through to the photosensitive surface. In this context, the limited angle of incidence range is preferably ≤20°, particularly preferably ≤10°.

A colour sensor that is manufactured using semiconductor technology is typically constructed from at least one photosensitive element, in particular a photodiode, and structured metallic layers as electrical contacts which are separated by dielectric layers. A colour filter is positioned over this layer stack, which stack consists of metal layers forming the metallic structures and dielectric layers. The colour filter may also be disposed below or inside the layer stack. Moreover, nanostructured metallic or dielectric layers with a colour filter effect may also be used as the colour filter, as is the case with the suggested colour sensor. In the suggested colour sensor, in order limit the angle of incidence of the radiation arriving at the colour sensor that reaches the photosensitive surface, an array of passageways is used which limit the angle of incidence according to their dimensioning. The use of an array of angle-selective passageways for each photosensitive element instead of a single passageway as is used in the prior art makes is possible to keep the height of the angle-selective structure low even with the large-area photosensitive elements used in colour sensors. This enables a colour sensor of such kind to be created with a correspondingly low height. The angle-selective passageways constitute regions through which the incident radiation can pass without significant losses if it enters the regions with an angle of incidence that lies within the limited angle of incidence range. These regions are limited by suitable structures which absorb or reflect the incident radiation in such manner that only a small part of it, if any, can pass through this region. In the following, the array of angle-selective passageways is also referred to as angle filter, the individual angle-selective passageways are also referred to as angle filter elements.

In general, the array may also be constructed in the form of an additional assembly above the layer stack. In the preferred variant, however, this array is integrated in the layer stack by structuring at least some of the metallic layers to form corresponding arrays of metallic apertures. At the same time, the individual apertures are each arranged one above the other so that they only allow light within a given angle of incidence range to reach the photosensitive surface of the photosensitive element.

Each passageway is designed to allow light fields with a correspondingly small angle of incidence to pass with as little attenuation as possible, and to attenuate light fields with larger angles of incidence as much as possible. The light that has been filtered out in this way must also not reach the photosensitive surface in the form of scattered or reflected light, instead it must be reflected back or absorbed beforehand. At the same time, the preferred variant of the suggested colour sensor does not use waveguides, but only scattering and absorption on correspondingly dimensioned metal structures. In this context, the angle-selective passageways are preferably formed not only by the metallic layers bur also by metal through-connections in the dielectric layers, which are appropriately designed and disposed for the purpose of limiting the angle of incidence.

In a preferred variant, the angle-selective passageways therefore comprise metal through-connections, also called "vias", in one or more dielectric layers of the layer stack, which are spread distributed around the central axes of the respective passageways. The bottom metallic aperture in each passageway, which is closest to the photosensitive surface and is formed in one of the lowest metallic layers of the layer stack, has an opening diameter that is smaller than the opening diameter of the apertures formed by the distribution of the metallic through-connections about the central axis. This makes it possible to achieve a particularly high degree of angle-selectivity, since radiation which is scattered back from the bottom aperture is absorbed by the metallic through-connections. The reason for the scattering and diffraction in the through-connections is because the dimensions thereof are smaller than the wavelength of the light in at least one dimension, having for example a diameter of approx. just 250 nm when 180 nm CMOS technology is used.

The array of passageways preferably comprises at least 3×3 elements or passageways over the photosensitive surface. The number of angle filter elements depends mainly on the size of the photosensitive surface and the required limitation of the angle of incidence. The centre-to-centre distances (pitch) of the individual angle filter elements or passageways are preferably between 1 and 12 µm for a lateral extent of the angle filter elements of preferably about 0.5 to 8 µm.

For the purposes of the present invention, the colour sensor is understood to mean not only a colour sensor with multiple colour channels or photosensitive elements which detect correspondingly different colour components and which are all furnished with a layer stack, a colour filter and an angle filter as described in the preceding description. On the contrary, the suggested colour sensor may also be designed as a primary colour sensor, which then only has one photosensitive element and only detects one colour range which is determined by the colour filter.

Colour sensors according to the present invention, which may also be designed as multispectrum sensors, may be used for example in colorimeters, for colour recognition in printing machines and the textile industry, to control the colour of LED lamps, or in analytics. This is not an exhaustive list. Because it is able to have a very low profile, an ultrathin colour sensor constructed in accordance with the present invention may very easily be integrated directly in a LED lamp or a smartphone.

BRIEF DESCRIPTION OF THE DRAWINGS

In the following, the suggested colour sensor will be explained again in greater detail with reference to exemplary embodiments thereof and in conjunction with the drawings. In the drawings.

WAYS OF REALISING THE INVENTION

Figure 1:
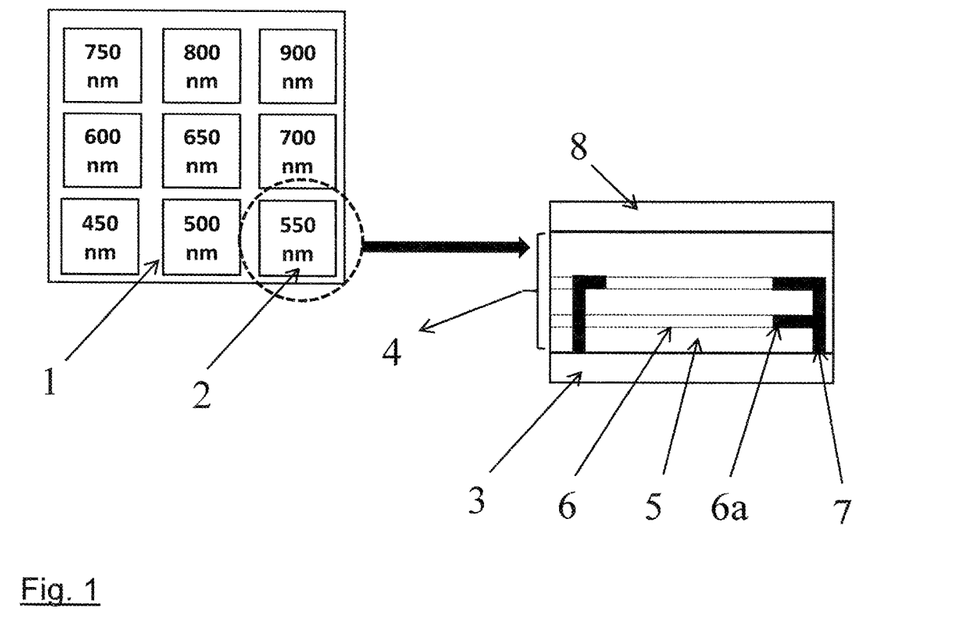
FIG. 1 shows an example of the structure of a colour sensor with nine colour channels.

An optical colour sensor usually includes a plurality of colour channels and colour sensor elements, which detect different spectral components of the incident incoming radiation. The diagram on the left in FIG. 1 shows a plan view of an example of an optical colour sensor 1 with nine colour sensor elements 2 for measuring chromaticity coordinate and colour temperature or estimating the spectrum of the incoming radiation. Each of these colour sensor elements 2 includes a large-area photodiode 3, a CMOS-layer stack 4 situated above the photodiode 3, and an optical colour filter 8. In the present example, each colour sensor element 2 is equipped with a different colour filter, as is indicated by the different wavelengths identified in the diagram on the left of the Figure, specifying the respective central passthrough wavelength (peak wavelength) of the colour filter. Photodiode 3 typically has a surface area ≥10×10 µm, to enable the high degree of sensitivity which is necessary in order to be able to measure chromaticity coordinate and colour temperature accurately. CMOS-layer stack 4 is furnished with vertical through-connections 7 and horizontal wiring 6a which is embedded in a dielectric material. This is a layer stack consisting of dielectric layers 5 and structured metallic layers 6, through which the horizontal wiring 6a is formed. Optionally, a microlens 9 may also be arranged on a colour sensor element 2, as is shown for exemplary purposes in FIGS. 2A and 2B. The suggested colour sensor may also be constructed in this manner.

Figure 2A:
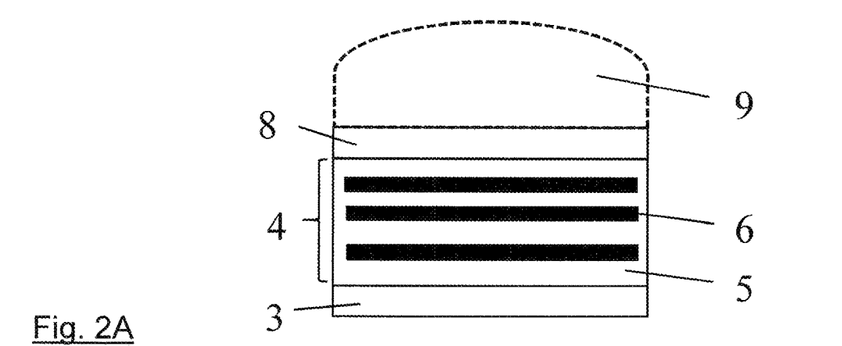
FIG. 2A shows an example of the structure of a colour sensor colour channel with top optical filter.
Figure 2B:
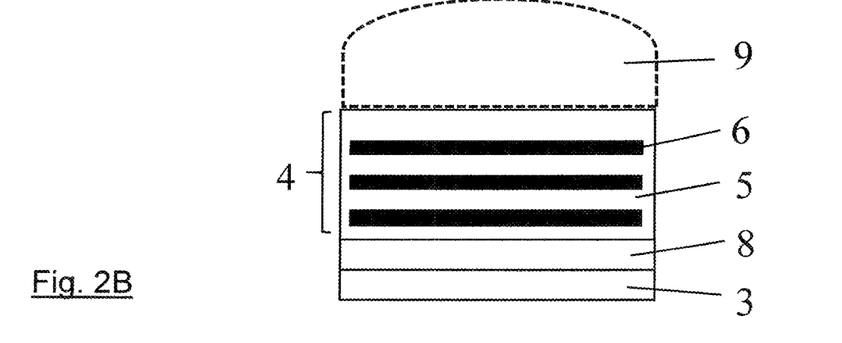
FIG. 2B shows an example of the structure of a colour sensor colour channel with bottom optical filter.

FIG. 2A shows an example of the structure of a colour sensor element with an optical filter 8 arranged above the CMOS-layer stack 4, and on top of which a microlens 9 is arranged. Optical filter 8, which is for example a nanostructured optical filter, may also be arranged between photodiode 3 and CMOS-layer stack 4, as is shown schematically in FIG. 2B. An arrangement between the individual layers 6 of CMOS-layer stack 4 is also possible.

Given the dependency of the colour filter on angle, in order to be able to measure colour accurately, the angle of incidence of the radiation that reaches the photodiode and which is detected by the photodiode must be very limited. For this purpose according to the prior art a mechanical structure is mounted on the sensor element, for example, as is shown schematically in FIG. 3. This angle-selective structure is constructed in the form of a cylinder 11 with two apertures 10. The ratio between the diameters of the apertures 10 and the height b of cylinder 11 defines the receiving angle of the incoming radiation. However, the angle of incidence of ≤10° which is usually necessary for the large-area photodiodes used in colour sensors means that height b of this structure must be selected to be much greater then thickness c of the sensor element. Accordingly, a colour sensor element with a CMOS-layer stack which is produced with semiconductor technology can be created with a thickness c of about 10 µm, whereas the height b of the mechanical structure for the requisite angle-selectivity is about 10 mm. Colour sensors and colour sensor elements of such kind therefore cannot be used for a high number of applications which require a correspondingly low profile of the colour sensor.

Figure 3:
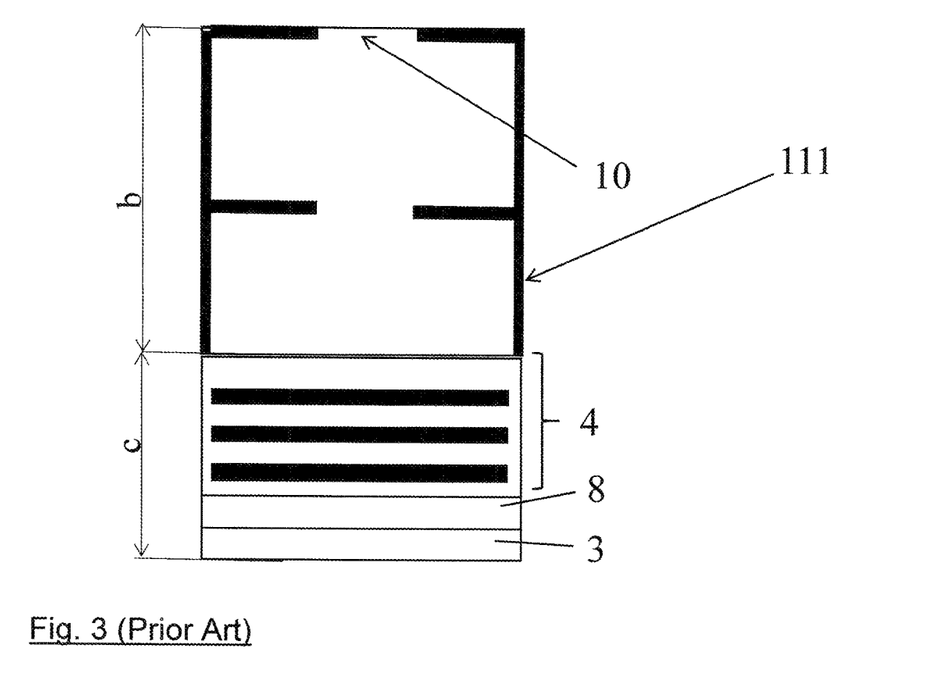
FIG. 3 shows an example of the structure of a colour sensor with angle-selective structure according to the prior art.
Figure 4A:
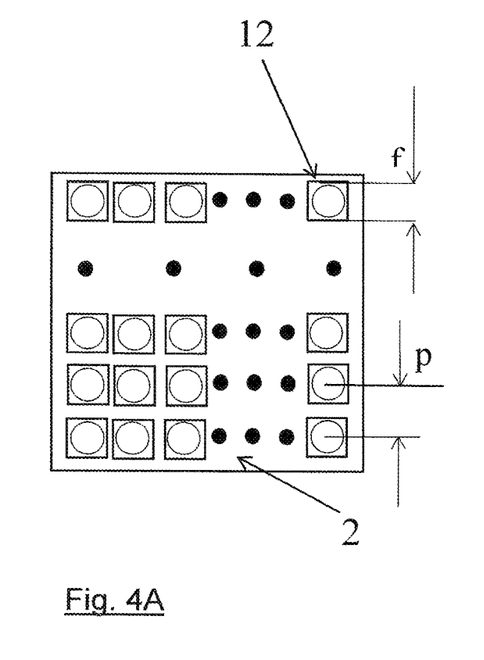
FIG. 4A is a plan view of an example of the suggested colour sensor structure.

This problem is solved with the suggested colour sensor in that an array of angle-selective passthrough channels or passageways—also called angle filters in the following—is used for each colour sensor element, i.e. each photodiode. For this purpose, FIG. 4A shows a plan view of an example of a corresponding colour sensor element 2 which includes such an array of angle-selective passageways or angle filter elements 12 above the photodiode. Through the use of not one individual angle-selective passageway, as shown in FIG. 3, but of an array of angle-selective passageways, the height of a corresponding structure may be reduced significantly compared with that of the prior art. In a preferred variant, this array of angle-selective passageways or angle filter elements may therefore also be integrated in CMOS-layer stack 4.

Figure 4B:
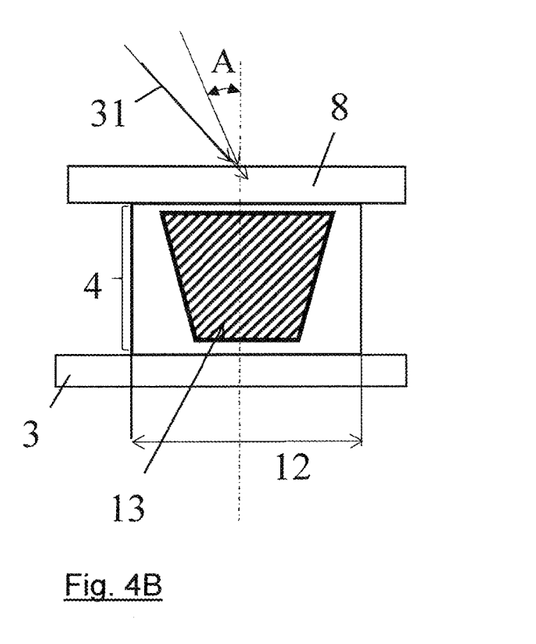
FIG. 4B shows a cross section of a first example of the structure of a passageway of the suggested colour sensor.

One possible way to realise this is to use the technology of the crosstalk filters known from the prior art of image sensor arrays, but in this case not to avoid crosstalk, but rather to limit the angle of incidence within a colour sensor element. Accordingly, FIG. 4B shows a cross section through an exemplary configuration of an angle filter element 12, which is formed by an optical waveguide in the CMOS-layer stack, the cross section of which tapers conically towards photodiode 3. A cylindrical waveguide may be used. In this example, the refractive index of the waveguide material is greater than the refractive index of the surrounding dielectric material. Each such waveguide may also be constructed with reflective or absorbent walls. The technology for embedding such waveguides in a CMOS-layer stack is described for example in US 2014/0197301 A1 cited earlier. Metal cylinders may also be used as waveguides, which may also be formed by through-connections which are radially closed about the central axis of the passageway. In this case, materials must be selected or an absorbent coating applied to prevent undesirable beam components from reaching the sensitive surface by reflection from the internal surface of the cylinders.

Figure 4C:
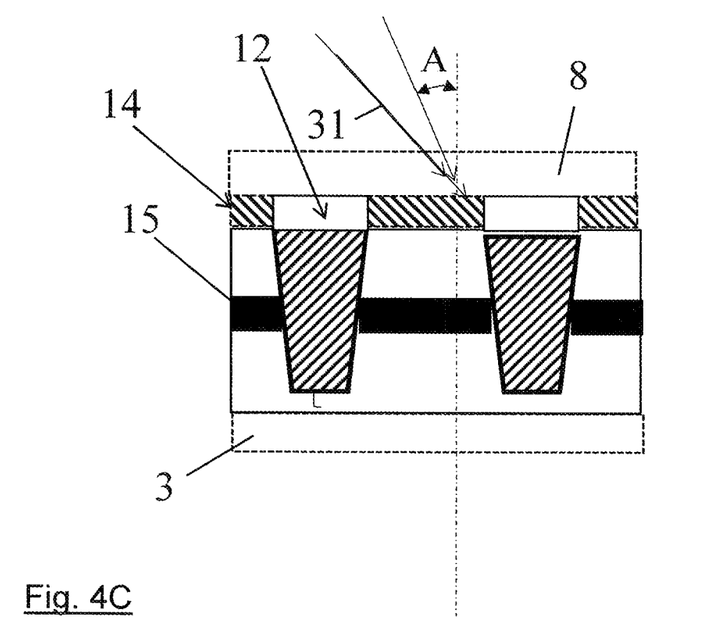
FIG. 4C shows a cross section of a second example of the structure of a passageway of the suggested colour sensor.
Figure 4D:
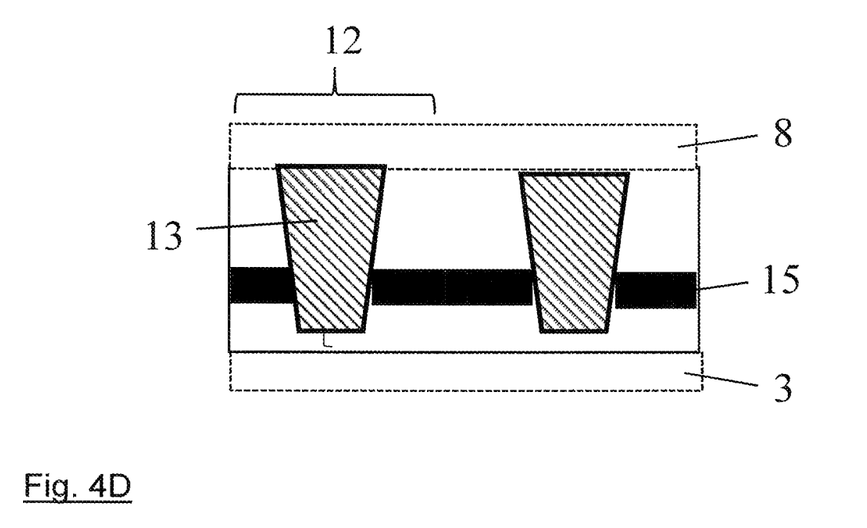
FIG. 4D shows a cross section of a third example of the structure of a passageway of the suggested colour sensor.

The spaces between the individual waveguides 13 may be covered with corresponding metallic structures in the metallic layers of the CMOS-layer stack 4, as is indicated in FIG. 4C with the two metal structures 14, 15. The top metallic structure 14 may also be a structured metallisation placed additionally over the CMOS-layer stack. FIG. 4D shows an exemplary embodiment in which a metallic structure 15 is disposed only in the lower region of the CMOS layer stack to cover the active surface of photodiode 3.

An incident beam 31 with an angle of incidence<A passes through the respective angle filter element 12 almost without attenuation and reaches photodiode 3. A beam 31 with an angle of incidence>A would be absorbed or reflected due to the properties of waveguide 13 (cf.FIGS 4B and 4C). An array consisting of such angle filter elements 12 may be arranged in front of colour filter 8 or behind colour filter 8 in the direction of the beam. The array must cover the active or sensitive surface of photodiode 3 completely. It has a centre-to-centre distance or pitch p between individual angle filter elements 12 which is equal to or greater than size f of each individual angle filter element (cf. FIG. 4A).

The ratio between the period or pitch p of the array and the element size f defines the transmittance and quality of the filtering. The space between the individual passageways or angle filter elements must be covered with metallic structures. If the array has a larger pitch p, the filter effect is improved but transmittance is poorer, and vice versa. The transmittance of the suggested angle filter in the acceptance range of the angle filter (e.g., +/−5° for plasmonic filters) is between 5% and 30%. Consequently, the available signal (photocurrent) is reduced by the same factor. In many applications in lighting technology, only low sample rates are needed, so the reduction in sensor sensitivity associated with the use of the angle filter can be compensated for by using an integrating preamplifier with longer integration times. The integration time for the preamplifier preferably is between 1 millisecond and 10 seconds. In applications with higher sampling rates, the damping of the angle filter can be compensated by increasing the surface areas of the photodiode or by increasing the amplification factor of the preamplifier.

The CMOS-layer stack 4 in colour sensors varies from process to process. Regardless of this, however, the array period of the suggested angle filter is preferably in the range between 0.5 and 10 μm. The optimum for size f of the angle filter elements is between 0.5 and 8 μm.

Figure 5A:
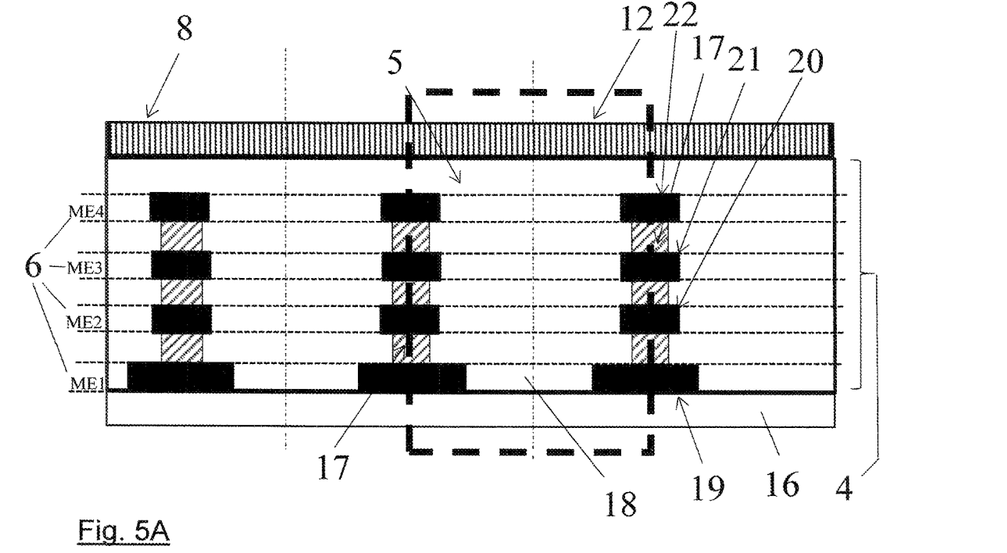
FIG. 5A shows a cross section of a fourth example of the structure of a passageway of the suggested colour sensor.

In the following, preferred variants of the suggested colour sensor and the angle-selective structures included therein will be explained. For this purpose, FIG. 5A shows an exemplary construction of a part of a colour sensor element with two angle filter elements 12 arranged side by side. In this example, an angle filter element is furnished with one or more rows of through-connections 17 in the dielectric layers 5 of CMOS-layer stack 4, an opening 18 in the bottom metallic layer 19 of layer stack 4, and metallic structures 20, 21, 22 realised as islands or rings in other metal layers (ME layers) from the bottom metallisation to the top metallisation. These metallic structures together form an angle-selective passageway to the photodiode in Si-substrate 16.

Figure 5B:
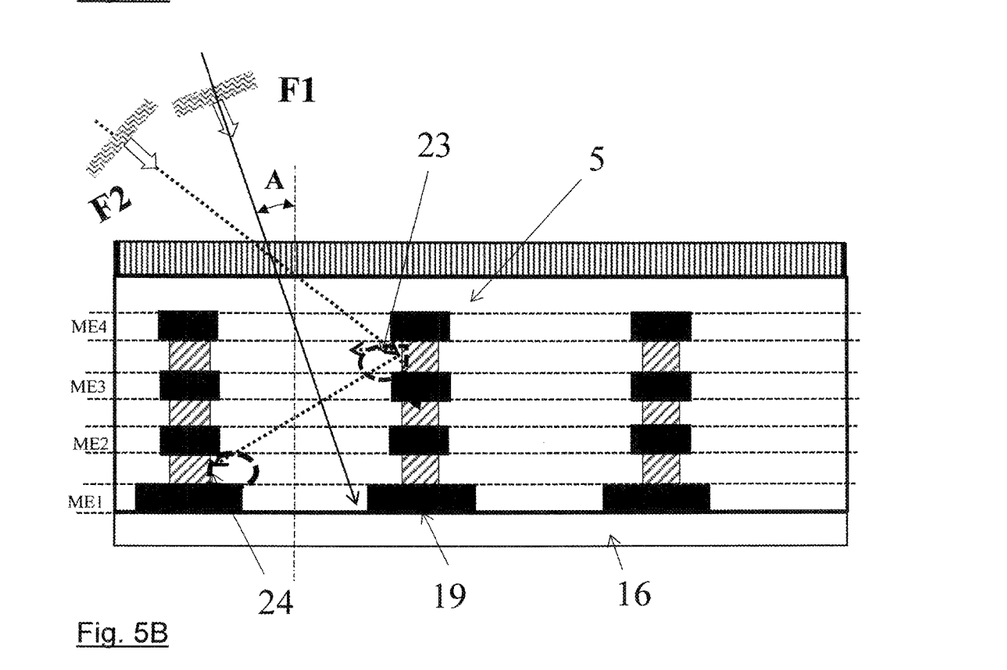
FIG. 5B is a schematic representation of the operating principle of the angle-selective structures of the suggested colour sensor.

The colour sensor element as a whole comprises an array of these passageways or angle filter elements 12. The size of an angle filter element is in the range from 0.5 to 10 μm. Given such a small size, geometric optics cannot be used for a simulation. Instead, the field propagation must be calculated. In practice, an angle filter element may be even larger than 10 μm. Field F1 with angle of incidence A, which is still acceptable for the angle filter, is only weakly diffracted by the several openings in the CMOS layers and passes through the opening 18 in the bottom metallic layer 19 to reach the photodiode in Si-substrate 16, as is indicated schematically in FIG. 5B. Field F2, which arrives at the light input side of the colour sensor element with a larger angle of incidence, encounters the row of through-connections 17 at the incidence position 23 indicated in FIG. 5B, where it is strongly diffracted and partly reflected, and propagates further as far as the next incidence position 24. There, it is strongly diffracted and reflected again on a row of through-connections 17 and then impinges on bottom metallic layer 19. What is left of field F2 is then reflected back upwards by this metal, so that it does not reach the photodiode 3 in substrate 16. If tungsten is used as the material for the through-connections 17 in the dielectric layers, the reflectance value at a wavelength of 587 nm is about 50%, the remaining energy component is absorbed. The reflectance value for aluminum, from which metallic structures 19-22 may be formed, for example, is 95%. Due to the multiple reflections and diffractions at the vias field F2 is attenuated to a much greater degree than field F1. Thus for example, field F2 is already weakened by 75% by just two reflections on through-connections 17.

In any semiconductor process design rules must be adhered to that define the minimum distance between through-connections. In order to realise the suggested angle filter, it is preferable to select the smallest permissible distance between the through-connections, because the smaller the distance is between the through-connections the greater the diffraction they cause, which increases the efficiency of angle filters without additional damping.

FIG. 6 again shows a construction of an angle filter element of the same kind in a cross section perpendicular to the surface of the photodiode and along cross sectional lines A-A and B-B, which correspond to the planes of metallic layers ME1 and ME4. In these layers, through-connections 17 are shown arranged around the passageway. For these through-connections 17 a material other can tungsten with strong attenuation or scattering effects for the incident radiation may also be used. In the same way, the apertures formed by the metallic structures in the metallic layers do not necessarily have to be made of aluminum, they may also consist of another metal.

Figure 6:
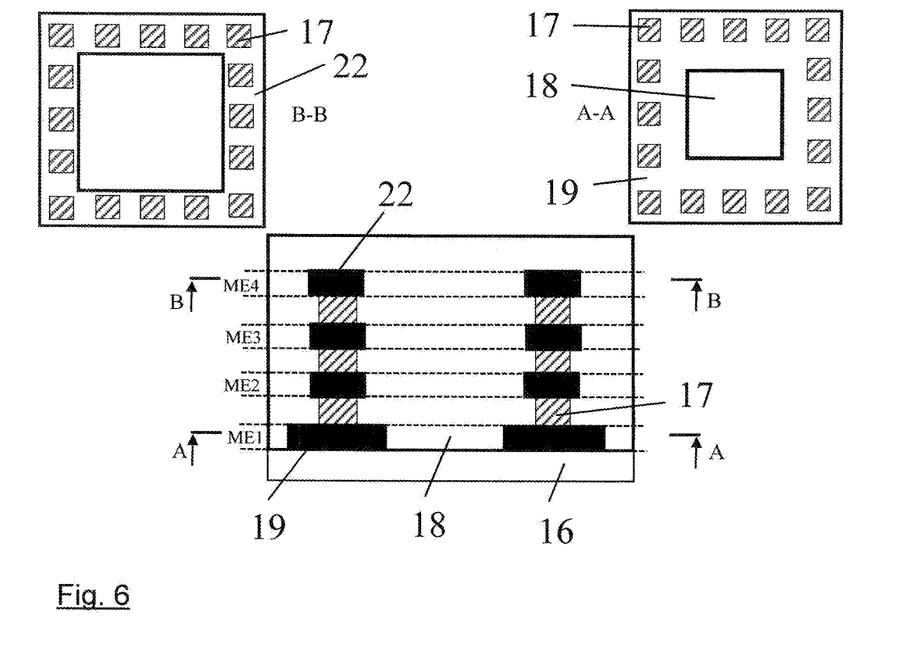
FIG. 6 is an example of the configuration of metallic apertures and the arrangement of the through-connections of a passageway in the suggested colour sensor.

In this example, opening 18 in metallic layer 19 (ME1) has a diameter of about 0.3 to 4 μm. This diameter depends on the size of the angle filter element and the wavelength. The period (pitch p) of the array is in the range from 1 to 12 μm. If pitch p is increased, the angle filter effect is improved, but the perpendicularly incident light is also attenuated to a greater degree due to the less optimal ratio of aperture opening 18 to the photosensitive surface.

Figure 7A:
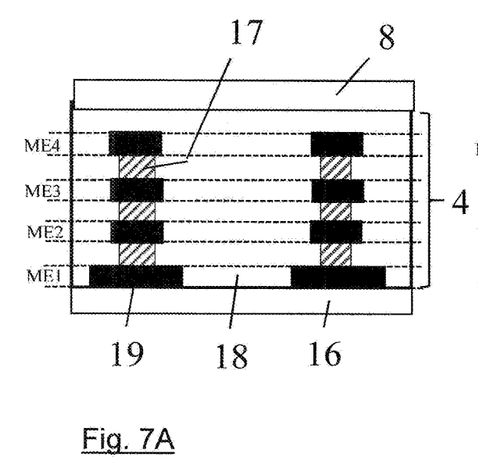
FIGS. 7A/B show two examples of the structure of a passageway in the suggested colour sensor.
Figure 7B:
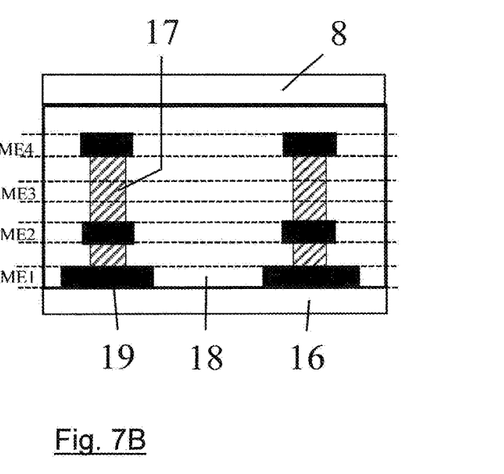

The suggested variant with multiple reflecting surfaces with a higher reflectance in the form of the structured metallic layers and rows of through-connections with low reflectance and a centre-to-centre distance of the through-connections which is smaller than the wavelength of the incident radiation has an advantage over variants in which closed, for example annular through-connections are arranged around the passageway. In the suggested design, three effects have the greatest influence on the attenuation associated with the angle of incidence. These are absorption by the material itself, the strong diffraction of a finer arrangement of the through-connections, and the scattering and diffraction caused by the metallic structures of the metallic layers ME2 up to the top metal. The structures in the metallic layers are arranged between the passageways. They may be arranged in a regular pattern, as shown in FIG. 7A or an irregular pattern as shown for exemplary purposes in FIG. 7B. A corresponding row of closely spaced individual through-connections is more effective than a metallic annular waveguide.

An angle filter should respond as neutrally as possible to wavelength. In the suggested arrangement, the smallest opening in each angle filter element should therefore preferably be close to the photodiode in order to eliminate the diffractive effects at this opening which are dependent on the wavelength. If wavelength-dependent effects do occur, for example wavelength-dependent attenuation, the angle filter may also be calibrated together with the colour filter to compensate for possible colour errors.

The application of angle filters in colour sensors that use a nanostructured optical colour filter is particularly important. Optical nanostructures in the dielectric material or in the metal are extremely sensitive to the angle of incidence. An angle of incidence of just 5° widens the bandpass filter on a hole array basis by 20% and reduces filter transmittance by 25%.

Figure 8:
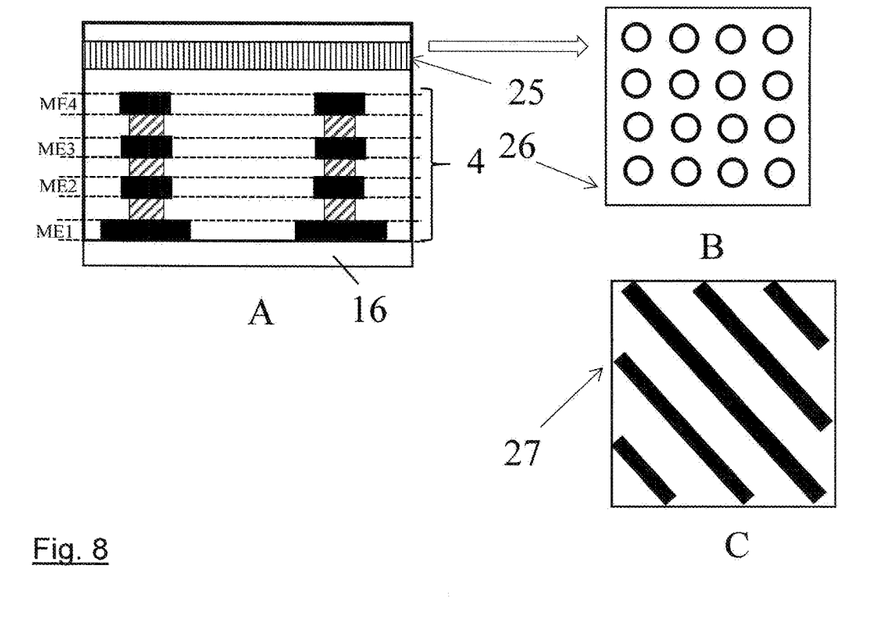
FIG. 8 shows two examples of the configuration of the colour filter in the suggested colour sensor.

FIG. 8 is a detail of an example of such a colour sensor element with a structured ME layer 25 on top. This may be a hole array or an island array 26, or a combination of several nanostructured layers integrated in the CMOS-layer stack. It may also be a polarisation filter 27 with ridges of metal or a dielectric material. Such filters of nanostructured layers may be located on top of the angle filter, as shown in FIG. 8, integrated in the CMOS layer stack (between the ME layers) or arranged below the angle filter, that is to say between the bottom metallic layer ME1 and photodiode 3 or Si-substrate 16. The angle filter filters out the light which reaches the filter at too great an angle and is to be regarded as interference light for the nanostructured filter(s).

Figure 9A:
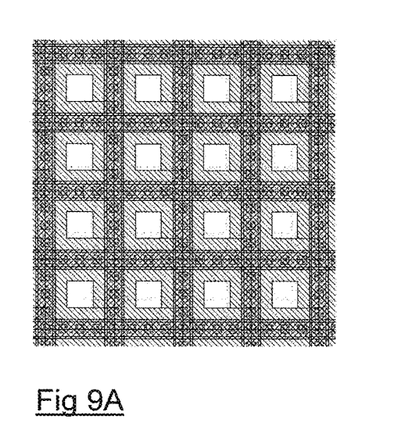
FIGS. 9A-C show an example of the configuration of the angle-selective structures of the suggested colour sensor in plan view.
Figure 9B:
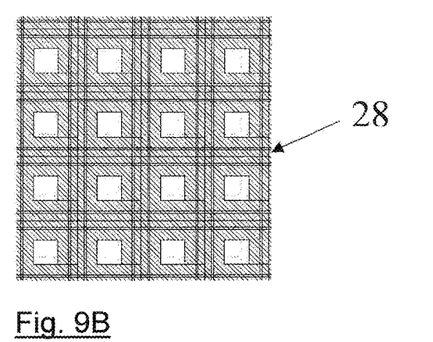
Figure 9C:
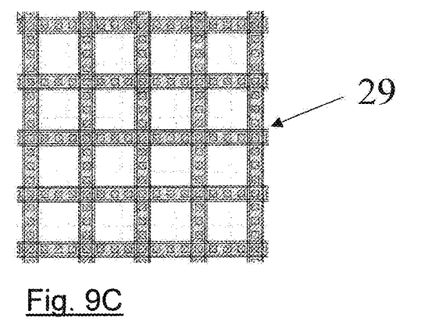

FIG. 9 shows a detail of a layout for the construction of an angle filter according to the present invention. In FIG. 9A, layers ME1 and ME2 and the through-connections are visible. FIG. 9B shows only ME1 layer 28 with openings, FIG. 9C shows ME2 layer 29 with the through-connections or vias. Although the through-connections are shown with a square cross section in the figures, they can have any cross sectional shape, for example they may be made round and/or without any straight edges during manufacturing.

Figure 10:
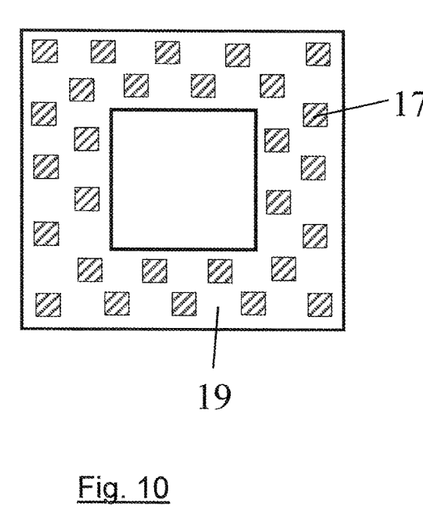
FIG. 10 shows an example of the distribution of the through-connections about the central axis of the passageway in the suggested colour sensor.
Figure 11:
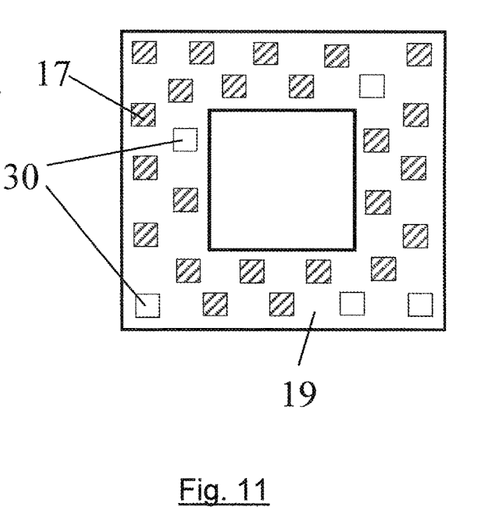
FIG. 11 shows a further example of the distribution of the through-connections about the central axis of the passageway in the suggested colour sensor.

Through-connections 17 may be distributed variously. FIG. 10 shows one example of the distribution. Multiple rows of through-connections 17 may be implemented about the central opening to increase the efficiency of the angle filter. Along with improved efficiency, however, the filter's transmittance is reduced. In this context, through-connections 17 may be arranged regularly in two rows, for example as shown in FIG. 10, or also irregularly. Of course, all kinds of other arrangements of the through-connections, also in more than two rows, are possible. One or more rows of through-connections with discontinuous symmetry are also possible. Such a design increases transmittance without sacrificing filter efficiency. In this regard, FIG. 11 shows an exemplary arrangement of two rows of through-connections 17, in which individual through-connections needed for a regular arrangement are missing. The positions of these missing through-connections 30 are indicated in the figure. If a still smaller number of through-connections is used, transmittance increases but the efficiency of the angle filter deteriorates.

The angle filter in the suggested colour sensor can be directly produced in semiconductor technology. Such colour sensors are significantly smaller, most importantly flatter, than colour sensors with an external mechanical buildup. An array-based angle filter is a solution for larger area colour sensors. The surface of the colour channel or colour sensor element of the colour sensor may thus be increased without deterioration of the angle filter function. The use of the angle filter together with plasmonic metal filters, which are highly sensitive to the angle of incidence, has the advantage that the entire colour sensor can be manufactured without postprocessing. It is thus possible to create ultra-flat colour sensors which do not require an external mechanical buildup. Since the colour filter spectrum is not highly dependent on the angle, the suggested angle filter is able to increase sensor resolution (spectral selectivity).

LIST OF REFERENCE SIGNS

1 Colour sensor
2 Colour sensor element
3 Photodiode
4 CMOS layer stack
5 Dielectric layer
6 Structured metallic layer
6a Horizontal wiring
7 Through-connection
8 Colour filter
9 Microlens
10 Aperture
11 Cylindrical structure
12 Angle filter element/Passageway
13 Waveguide
14 Structured metallisation
15 Structured metallic layer
16 Si-substrate with photodiode
17 Through-connection
18 Opening
19 Bottom metallic layer
20 Metallic structure
21 Metallic structure
22 Metallic structure
23 Incidence position
24 Incidence position
25 Nanostructured colour filter
26 Hole or island array
27 Polarisation filter
28 ME1 layer
29 ME2 layer with through-connections
30 Missing through-connection
31 Incident beam

The invention claimed is:

1. Colour sensor having at least one photosensitive element, in front of which a layer stack of dielectric layers and structured metal layers is formed, and at least one colour filter, through which optical radiation incident on a light input side of the colour sensor is filtered before it reaches a photosensitive surface of the photosensitive element,
   characterised in that
   an array of angle-selective passageways is provided for the optical radiation, between the light input side and the photosensitive surface for each of said at least one photosensitive element, and each passageway only allows parts of the optical radiation incident on the light input side of the colour sensor within a limited angle of incidence range relative to an axis extending perpendicularly to the colour filter to pass through to the photosensitive surface.

2. Colour sensor according to claim 1,
   characterised in that
   the angle-selective passageways are formed by metallic structures in the layer stack.

3. Colour sensor according to claim 1, characterised in that
the angle-selective passageways each comprise metallic apertures which are formed in several of the structured metallic layers.

4. Colour sensor according to claim 3, characterised in that
the angle-selective passageways each comprise metallic through-connections in one or more of the dielectric layers, which are distributed around central axes of the passageways, wherein an opening diameter of a lowest of the metallic apertures, which is closest to the photosensitive surface, is smaller in each case than the opening diameter of the openings created by the distribution of the metallic through-connections about the central axis.

5. Colour sensor according to claim 4, characterised in that
the metallic through-connections are arranged in at least one row about the central axes of the passageways, in which they are spaced with a centre-to-centre distance that is smaller than 1 μm.

6. Colour sensor according to claim 5, characterized in that the metallic through-connections are spaced with a centre-to-centre distance that is smaller than 0.5 μm.

7. Colour sensor according to claim 1, characterised in that
the angle-selective passageways each comprise metallic through-connections in one or more of the dielectric layers.

8. Colour sensor according to claim 1, characterised in that
the photosensitive surface has a size of ≥10×10 μm.

9. Colour sensor according to claim 1, characterised in that
the array consists of at least 3×3 passageways.

10. Colour sensor according to claim 1, characterised in that
the colour sensor is produced with semiconductor technology.

11. Colour sensor according to claim 10, characterized in that the colour sensor is produced with CMOS technology.

12. Colour sensor according to claim 1, characterised in that
the photosensitive element is a photodiode.

13. Colour sensor according to claim 1, characterised in that
the colour filter is an interference filter or a nanostructured filter.

14. Colour sensor according to claim 1, characterised in that
the colour sensor includes at least one integrating preamplifier which is connected to one or more of the photosensitive elements.

15. Colour sensor according to claim 14, characterised in that
the integrating preamplifier has an integration time in the range between 1 millisecond and 10 seconds.

* * * * *